US008187583B2

(12) United States Patent
Hedges et al.

(10) Patent No.: US 8,187,583 B2
(45) Date of Patent: May 29, 2012

(54) OIL-IN-WATER EMULSIONS

(75) Inventors: Nicholas David Hedges, Sharnbrook (GB); John Turner Mitchell, Sharnbrook (GB); Gleb Yakubov, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/694,325

(22) Filed: Jan. 27, 2010

(65) Prior Publication Data
US 2010/0197810 A1  Aug. 5, 2010

(30) Foreign Application Priority Data

Jan. 30, 2009 (EP) .................................... 09151786

(51) Int. Cl.
A61K 31/00 (2006.01)
A61K 8/02 (2006.01)
A61K 9/16 (2006.01)
A23L 1/00 (2006.01)

(52) U.S. Cl. .................. 424/78.13; 424/401; 424/493; 424/494; 424/498; 426/98; 426/303

(58) Field of Classification Search .................. None
See application file for complete search history.

(56) References Cited

U.S. PATENT DOCUMENTS

| 6,234,464 | B1 | 5/2001 | Krumbholz et al. | 264/4.32 |
| 2001/0008874 | A1* | 7/2001 | Igari et al. | 504/359 |
| 2005/0067726 | A1 | 3/2005 | Yan et al. | 264/4.1 |
| 2006/0222851 | A1 | 10/2006 | Miyabayashi et al. | 428/408 |
| 2007/0003628 | A1* | 1/2007 | Liversidge et al. | 424/489 |
| 2007/0104866 | A1* | 5/2007 | McClements et al. | 427/213.3 |
| 2009/0041816 | A1* | 2/2009 | Dotsenko et al. | 424/401 |

FOREIGN PATENT DOCUMENTS

| DE | 1817316 | 12/1969 |
| DE | 10037707 | 2/2002 |
| EP | 1 647 326 | 3/1999 |
| GB | 1 257 178 | 12/1971 |
| GB | 2 324 457 | 10/1998 |
| WO | 02/09865 | 2/2002 |
| WO | 03/018186 | 3/2003 |
| WO | 03/082313 | 10/2003 |
| WO | 2004/069169 | 8/2004 |
| WO | 2005/084458 | 9/2005 |
| WO | 2007/023495 | 3/2007 |
| WO | 2007/085840 | 8/2007 |
| WO | 2008/037578 | 4/2008 |
| WO | 2010/086235 | 8/2010 |

OTHER PUBLICATIONS

PCT International Search Report in PCT application PCT/EP2010/0504450, dated Mar. 25, 2010.
European Search Report—EP 07 11 3633, dated Jan. 10, 2008.
PCT International Search Report in PCT application PCT/EP2008/059714, filed Oct. 16, 2008.
Abstract of EP 1 647 326 published Mar. 19, 1999.
Abstract of DE 10037707—published Feb. 14, 2002.
Baker et al., "Sugar Fatty Acid Ester Surfactants: Base-Catalyzed Hydrolysis", Journal of Surfactants and Detergents, vol. 3, No. 1, 2000, pp. 29-32.
Hagerstrom, "Polymer Gels as Pharmaceutical Dosage Forms", Comprehensive Summaries of Uppsala Dissertations from the Faculty of Pharmacy 293, pp. 1-76 (2003).
Sisterna® Sucrose Esters General Information pp. 1-12 (undated brochure).
Sogias et al., "Why is Chitosan Mucoadhesive?", Biomacromolecules, 2008, vol. 9, pp. 1837-1842.
Smart, "The basics and underlying mechanisms of mucoadhesion," Advanced Drug Deliver Reviews, 2005, vol. 57, pp. 1556-1568.
Co-pending Application: Applicant: Dotsenko et al., U.S. Appl. No. 12/220,981, filed Jul. 30, 2008.

* cited by examiner

*Primary Examiner* — Robert A Wax
*Assistant Examiner* — Jeffrey T Palenik
(74) *Attorney, Agent, or Firm* — Karen E. Klumas

(57) ABSTRACT

Improved oil-in-water emulsions are provided and a method for their manufacture. In particular, the emulsions comprise a means to control delivery of oil-soluble or water-soluble actives in a core comprising a liquid oil or gel oil continuous phase, which actives can be delivered with improved deposition to surfaces such as, in particular, the skin, gastro-intestinal tract and that defined by the oral cavity. The emulsions are also noted for their improved stability.

The stable emulsion comprises a stable droplet dispersed in an aqueous phase, the stable droplet comprising a core, a first inner layer coating the core, and a second outer layer coating the first inner layer, wherein the core comprises at least a liquid oil or gel oil continuous phase, wherein the first inner layer comprises at least one at least partially solid uncharged emulsifier and at least one anionic or cationic or zwitterionic emulsifier, the second outer layer comprises a first polycation or first polyanion or first polyzwitterion of opposing charge to the first inner layer, and wherein the at least partially solid uncharged emulsifier forms a solution in the aqueous phase or the liquid oil phase or the gel oil phase at temperatures greater than room temperature, preferably greater than 40, more preferably greater than 50, even more preferably greater than 60 degrees centigrade.

The invention also provides a product selected from the group consisting of a food product, a home care product, a personal care product and a pharmaceutical product, wherein each product comprises emulsion of the invention.

15 Claims, 4 Drawing Sheets

OIL-IN-WATER EMULSIONS

Improved oil-in-water emulsions are provided and a method for their manufacture. In particular, the emulsions comprise a means to control delivery of oil-soluble or water-soluble actives in a core comprising a liquid oil or gel oil continuous phase, which actives can be delivered with improved deposition to surfaces such as, in particular, the skin, gastro-intestinal tract and that defined by the oral cavity. The emulsions are also noted for their improved stability.

BRIEF DESCRIPTION OF THE INVENTION

In a first aspect of the invention, a stable emulsion is provided comprising a droplet dispersed in an aqueous phase, the droplet comprising a core, a first inner layer coating the core, and a second outer layer coating the first inner layer, wherein the core comprises at least a liquid oil or gel oil continuous phase, wherein the first inner layer comprises at least one at least partially solid uncharged emulsifier and at least one anionic or cationic or zwitterionic emulsifier, the second outer layer comprises a first polycation or first polyanion or first polyzwitterion of opposing charge to the first inner layer, and wherein the at least partially solid uncharged emulsifier forms a solution in the aqueous phase or the liquid oil phase or the gel oil phase at temperatures greater than room temperature, preferably greater than 40, more preferably greater than 50, even more preferably greater than 60 degrees centigrade.

It is thought that the at least partially solid uncharged emulsifier must be uncharged so that it is less likely to remain dispersed in the aqueous phase and must be at least partially solid thereby to improve the stability of the emulsified liquid oil or gel oil phase by formation of a solid interface between the aqueous phase and liquid oil or gel oil phase. Preferably the uncharged emulsifier is solid and forms a solution in the aqueous phase or the liquid oil phase or the gel oil phase at temperatures greater than room temperature, preferably greater than 40, more preferably greater than 50, even more preferably greater than 60 degrees centigrade.

The release profile of actives from the core can be optimised for a given purpose by changing the composition of the first inner layer and the second outer layer. In particular the release profile may be tailored to respond to changes in temperature, salt levels, pH or the presence of particular enzymes present in, for example, the mouth. Thus the release profile may be optimised for sensorial reward or to improve efficacy, for example by enabling sustained release of an active, or to mitigate negative side-effects, such as skin irritancy, arising from a more intense release of an active over a shorter time period.

The core may have a largest dimension of 0.010 to 200 μm, preferably 0.050 to 30 μm and can adopt any shape, such as a sphere, a rod, a disc, as well as other ill-defined shapes. Preferably the core is spherical.

The combined thickness of the first inner layer and the second outer layer may be 0.001 to 0.500 μm and thus the largest dimension of the droplet may be 0.012 to 200.1 μm, preferably 0.052 to 31.0 μm. The thickness of the first inner layer and the second outer layer may be measured by using commonly known methods such as ellipsometry, dual polarisation interferometry, optical waveguide light spectroscopy, a quartz crystal microbalance, dynamic light scattering, atomic force microscopy (or other scratch test instruments using similar principles) or fluorescent confocal microscopy.

Usually a droplet comprises 0.001 to 99.999, preferably 10 to 99.999, more preferably 20 to 99.999, most preferably 50 to 99.999% by weight core based on the total weight of the droplet.

The core may be selected from the group consisting of a liquid oil, a gel oil, a water-in-liquid oil emulsion, a water-in-gel oil emulsion, a multiple emulsion wherein the continuous phase is a liquid oil or a gel oil, and a liquid oil or gel oil continuous phase dispersion. Thus oil-soluble actives can be carried in the liquid oil or gel oil phase and water-soluble actives may be carried in any aqueous phase within the droplet. Indeed both oil-soluble and water-soluble actives may be carried in the same droplet simultaneously.

The liquid oil or gel oil phase may be selected from the group consisting of vegetable oil, animal oil, mineral oil and synthetic oil. Preferred vegetable oils are coconut oil, corn oil, cottonseed oil, canola oil (rapeseed oil), olive oil, palm oil, peanut oil (ground nut oil), safflower oil, sesame oil, soybean oil, sunflower oil, almond oil, cashew oil, hazelnut oil, macadamia oil, pecan oil, pistachio oil, walnut oil, acai oil, blackcurrant seed oil, borage seed oil, evening primrose oil, carob seed pods, amaranth oil, apricot oil, argan oil, avocado oil, babassu oil, ben oil, carob pod oil (algaroba oil), coriander seed oil, false flax oil (made of the seeds of camelina sativa), coriander seed oil, hemp oil, kapok seed oil, meadowfoam seed oil, mustard oil (pressed), okra seed oil, perilla seed oil, pine seed oil, poppyseed oil, prune kernel oil, pumpkin seed oil, quinoa oil, ramtil oil, rice bran oil, tea oil (camellia oil), thistle oil, wheat germ oil, castor oil, radish oil, ramtil oil, allanblackia oil and tung oil. Preferred animal oils are tallow oil and fish oil (for example cod liver oil).

Preferably the at least partially solid uncharged emulsifier is at least partially crystalline. More preferably the at least partially solid uncharged emulsifier is selected from the group consisting of a sucrose ester, a (poly)-glycerol ester of a fatty acid and a sorbitan ester. In particular the sucrose ester may be of formula (I)

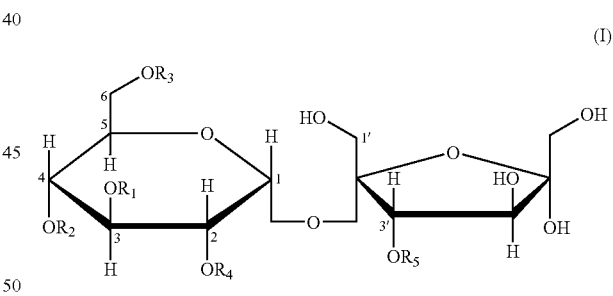

wherein $R_1$, $R_2$, $R_3$, $R_4$ and $R_5$ are independently from each other any non-toxic fatty acid radical, such as stearic acid, palmitic acid, oleic acid, lauric acid, erucic acid and other fatty acid radicals. Specific examples of suitable sucrose esters are mixtures of sucrose monostearate and sucrose distearate (especially the 70%:30% mixture) or mixtures of sucrose monopalmitate and sucrose dipalmitate.

The anionic emulsifier may be selected from the group consisting of stearic acid and palmitic acid. The cationic emulsifier may be selected from the group consisting of cetyl trimethylammonium chloride, cetylpyridinium chloride, benzethonium chloride, hydroxypropyl guar hydroxypropyl trimonium chloride (Jaguar C 162 available from Rhodia) and guar hydroxypropyl trimonium chloride (Jaguar C 13 S available from Rhodia). The zwitterionic emulsifier may be selected from the group consisting of a lecithin, cocamidopropyl betaine, dodecyl betaine and phosphatidylcholine. In use, the net charge of the zwitterionic emulsifier is controlled through pH to yield either a net negative (anionic) or net positive (cationic) charge.

In a preferred embodiment of the invention, the emulsion additionally comprises a third outer layer coating the second outer layer, the third outer layer comprising at least a second polyanion or at least a second polycation or at least a second polyzwitterion of opposing charge to the second outer layer. The coated particle may comprise more than three layers, for example at least four layers, with successive layers, in alternating fashion, comprising at least a polyanion or a polycation or a polyzwitterion, a fourth layer coating the third outer layer, wherein the fourth layer comprises a polyelectrolyte of opposing charge to the polyelectrolyte (second polyanion or second polycation or second polyzwitterion) of the third outermost layer. Preferably the coated particle comprises 2 to 20 layers, more preferably 3 to 20 layers, even more preferably 2 to 10 layers, most preferably 3 to 10 layers. The release profile of actives from the core can be optimised for a given purpose by varying the number of layers with additional layers typically slowing release.

By polyanion is meant a charged molecule with a net negative charge and at least two charged groups. By polycation is meant a charged molecule with a net positive charge and at least two charged groups. By polyzwitterion is meant a charged molecule with a net charge of at least two positive charges or two negative charges through manipulation of the pH. Thus the first polyanion and the second polyanion may be selected from the group consisting of alginate, carboxymethylamylose, carboxymethylcellulose, carboxymethyldextran, carageenan, cellulose sulphate, chrondroitin sulphate, chitosan sulphate, dextran sulphate, gum arabic, gellan gum, heparin, hyaluronic acid, pectin, amidated pectins, xanthan gum, proteins and glycoproteins. The first polycation and the second polycation may be selected from the group consisting of chitosan, modified dextrans, hydroxymethylcellulose trimethylamine, lysozyme, polylysine, protamine sulphate, hydroxyethylcellulose trimethylamine and proteins.

In a second aspect of the invention, a product is provided, the product selected from the group consisting of a food product, a home care product, a personal care product and a pharmaceutical product, wherein each product comprises the emulsion of the invention.

By food product is meant any food product for animals or humans though preferably for humans. Thus suitable food products include any kind of drink or other liquid food product, snacks, candies and confections, cookies, fillings, toppings, dessert mixes, granola bars, energy bars, shelf stable powders, puddings, yogurts, frozen yogurts, ice creams, cereals, meal replacements, baked goods, pasta products, military rations, specially formulated foods for children, mayonnaise, salad dressings, sauces, dips, creams, gravies, spreads, soups, coffee whiteners and desserts.

Home care products include laundry detergents and fabric softeners particularly when incorporating perfumes.

Personal care products include skin creams, soaps, soap bars, bath and shower gels, shampoos, mousses, deodorants, anti-perspirants, lipsticks, sunscreens and oral care products such as toothpastes and mouthwashes.

In a third aspect of the invention, a process for the manufacture of the emulsion of the invention is provided, the method comprising the steps of:
(a) emulsifying the liquid oil or gel oil phase in the aqueous phase with the at least one at least partially solid uncharged emulsifier thereby to form a solid interface between the two phases, wherein the at least one at least partially solid uncharged emulsifier is hydrolysable; then
(b) partially hydrolysing the at least one at least partially solid uncharged emulsifier thereby to form the at least one anionic or cationic or zwitterionic emulsifier thereby to form a core coated with the first inner layer; then
(c) washing the core coated with the first inner layer; and then
(d) applying the second outer layer to the first inner layer thereby to form an emulsion according to the invention.

In a fourth aspect of the invention, another process for the manufacture of the emulsion of the invention is provided, the process comprising the steps of:
(a) emulsifying the liquid oil or gel oil phase in the aqueous phase with the at least one at least partially solid uncharged emulsifier and the at least one anionic or cationic or zwitterionic emulsifier, thereby to form a solid interface between the two phases and, thereby to form a core coated with the first inner layer; then
(b) washing the core coated with the first inner layer; and then
(c) applying the second outer layer to the first inner layer thereby to form the emulsion of the invention.

In one embodiment of the invention, the processes for the manufacture of an emulsion according to the invention further comprise the steps of:
(a) washing the core coated with the first inner layer and second outer layer; then
(b) applying the third outer layer to the second outer layer thereby to form the emulsion of the invention; then optionally
(c) washing the core coated with the first inner layer, second outer layer and third outer layer; and then optionally
(d) repeating the application and washing steps for successive layers of polycation or polyanion or polyzwitterion The process of emulsifying the liquid oil or gel oil phase in the aqueous phase with the at least one at least partially solid uncharged emulsifier thereby to form a solid interface between the two phases can comprise the steps of:
(a) solubilising the at least one at least partially solid uncharged emulsifier in the aqueous phase or the liquid oil phase or the gel oil phase at temperatures greater than room temperature, preferably greater than 40, more preferably greater than 50, even more preferably greater than 60 degrees centigrade;
(b) combining the liquid oil or gel oil phase with the aqueous phase;
(c) emulsifying the liquid oil or gel oil phase in the aqueous phase at the temperature at which the at least one at least partially solid uncharged emulsifier remains in solution in the aqueous phase or the liquid oil phase or gel oil phase thereby to produce a base emulsion;
(d) cooling the base emulsion thereby to form a solid interface between the two phases;
wherein steps (a) and (b) may be reversed Electrophoretic measurements, by determining the zeta-potential or/and the surface charge of the partly or wholly formed droplets, are used to confirm the satisfactory presence of each layer and that the charge of each layer is alternating. The application step is carried out by immersing the partly formed droplet in an aqueous solution of the relevant polyelectrolyte. The degree of application of each layer can be controlled by varying the pH, the ionic composition of each solution, the temperature of each solution and ionic strength of each solution. The washing step is carried out in a washing liquor of water or an aqueous solution of appropriate pH and ionic strength followed by separation of the partly or wholly formed droplets from the washing liquor by, for instance, centrifugation. The amount of each layer can be controlled by varying the temperature of the washing liquor. The partly or wholly formed droplets may be subject to more than one wash.

BRIEF DESCRIPTION OF THE FIGURES

The invention will now be illustrated with reference to.

DETAILED DESCRIPTION OF THE INVENTION

Example 1

Thermal Properties of a Sugar Ester Mixed with Water

Figure 1A:
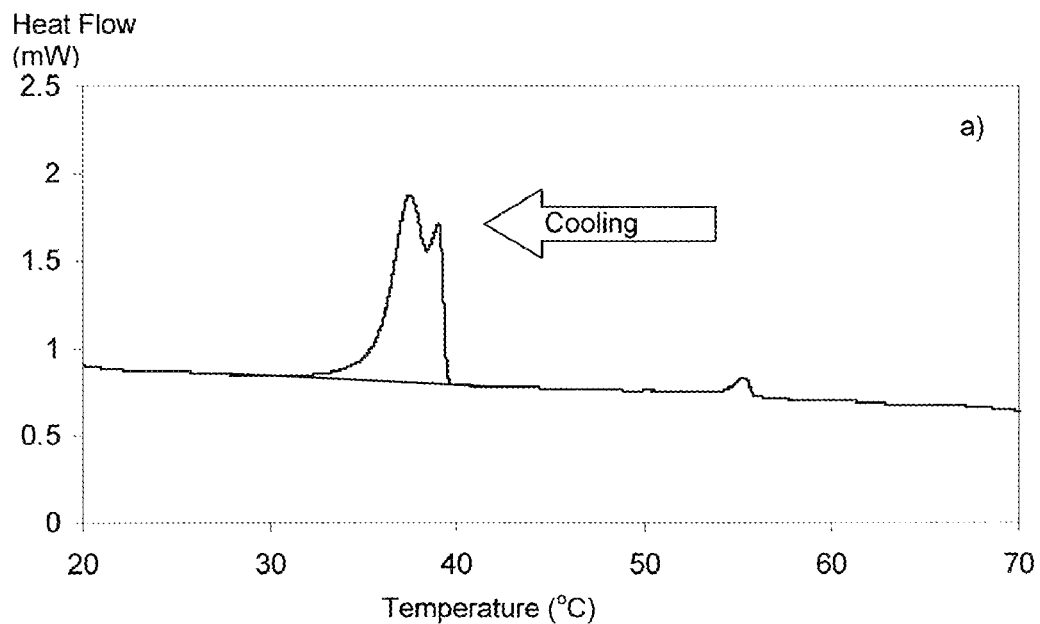
FIGS. 1a and 1b which show the cooling and subsequent heating behaviour respectively of a 5% w/w sugar ester (P-1670) aqueous dispersion using differential scanning calorimetry.
Figure 1B:
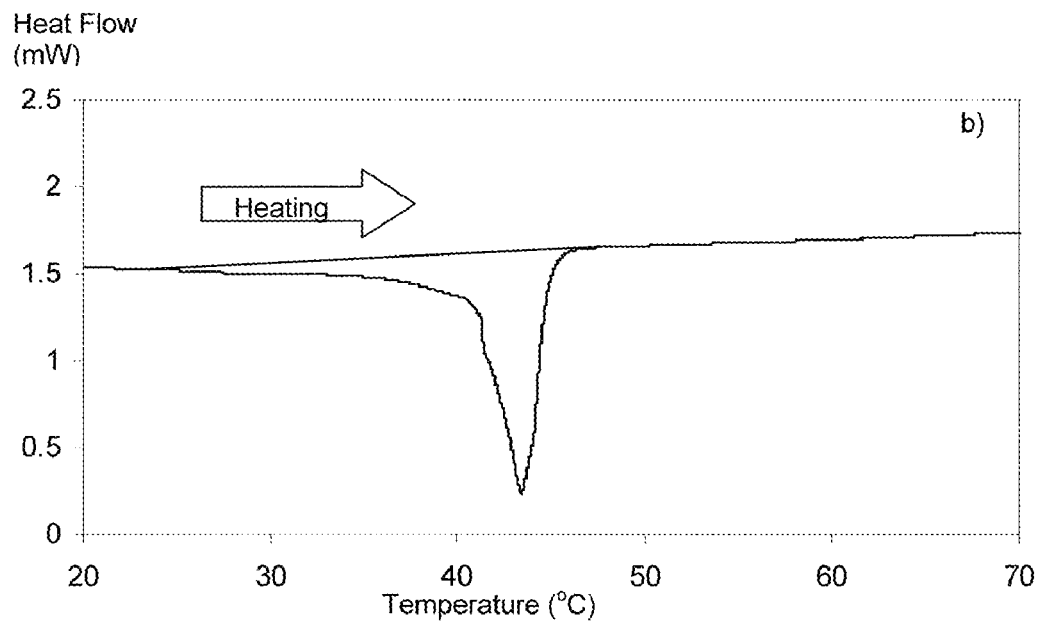

A 5% w/w sugar ester (Ryoto P-1670, Mitsubishi-Kagaku Foods Corporation, Japan) aqueous dispersion was prepared at room temperature. The dispersion was heated in a Setaram Micro DSC III differential scanning calorimeter. Approximately 0.7 g samples were loaded into 1 cm$^3$ stainless steel cuvettes and scanned over the temperature range 0 to 99° C. at a rate of 0.5° C./minute against a water reference. FIGS. 1a and 1b show the cooling and subsequent reheating curves respectively from which an exothermic event is observed on cooling as the sugar ester crystallises from solution (FIG. 1a) and an endothermic event is observed on heating as the sugar ester melts (FIG. 1b).

Example 2

Thermal Properties of a Commercial Monoglyceride Mixed with Water

Figure 2A:
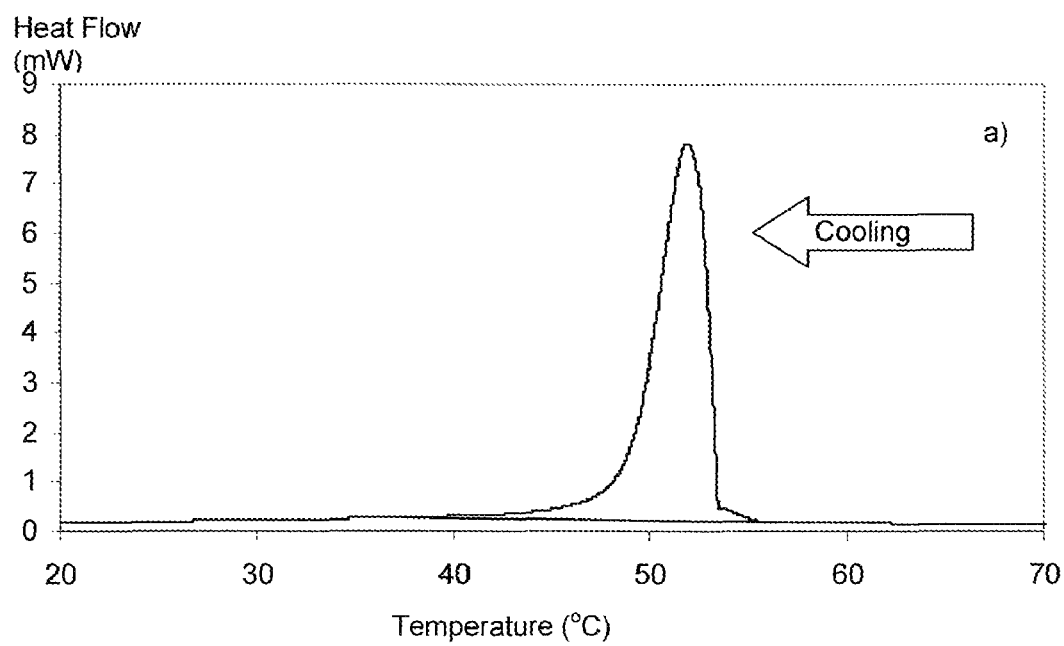
FIGS. 2a and 2b which show the cooling and subsequent heating behaviour respectively of a 5% w/w monoglyceride (Dimodan HP) aqueous dispersion using differential scanning calorimetry.
Figure 2B:
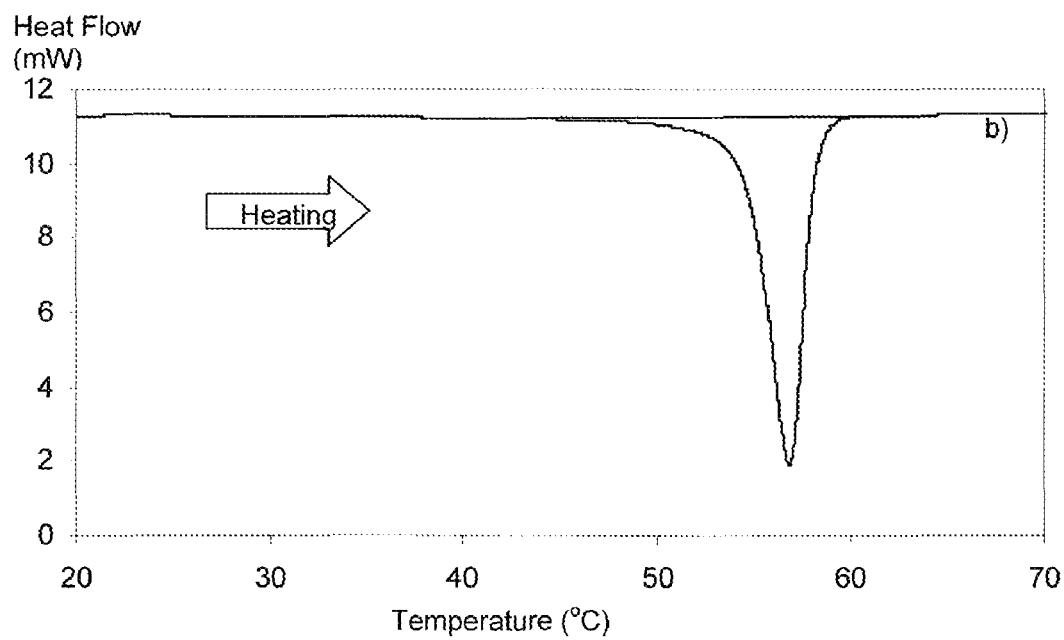

A 5% w/w monoglyceride (Dimodan HP, Danisco) aqueous dispersion was prepared at room temperature. The dispersion was heated in a Setaram Micro DSC III differential scanning calorimeter. Approximately 0.7 g samples were loaded into 1 cm$^3$ stainless steel cuvettes and scanned over the temperature range 0 to 99° C. at a rate of 0.5° C./minute against a water reference. FIGS. 2a and 2b show the cooling and subsequent reheating curves respectively from which an exothermic event is observed on cooling as the monoglyceride crystallises from solution (FIG. 2a) and an endothermic event is observed on heating as the monoglyceride melts (FIG. 2b)

Example 3

Thermal Properties of a Commercial Monoglyceride Mixed with Sunflower Oil

Figures 3A, 3B:
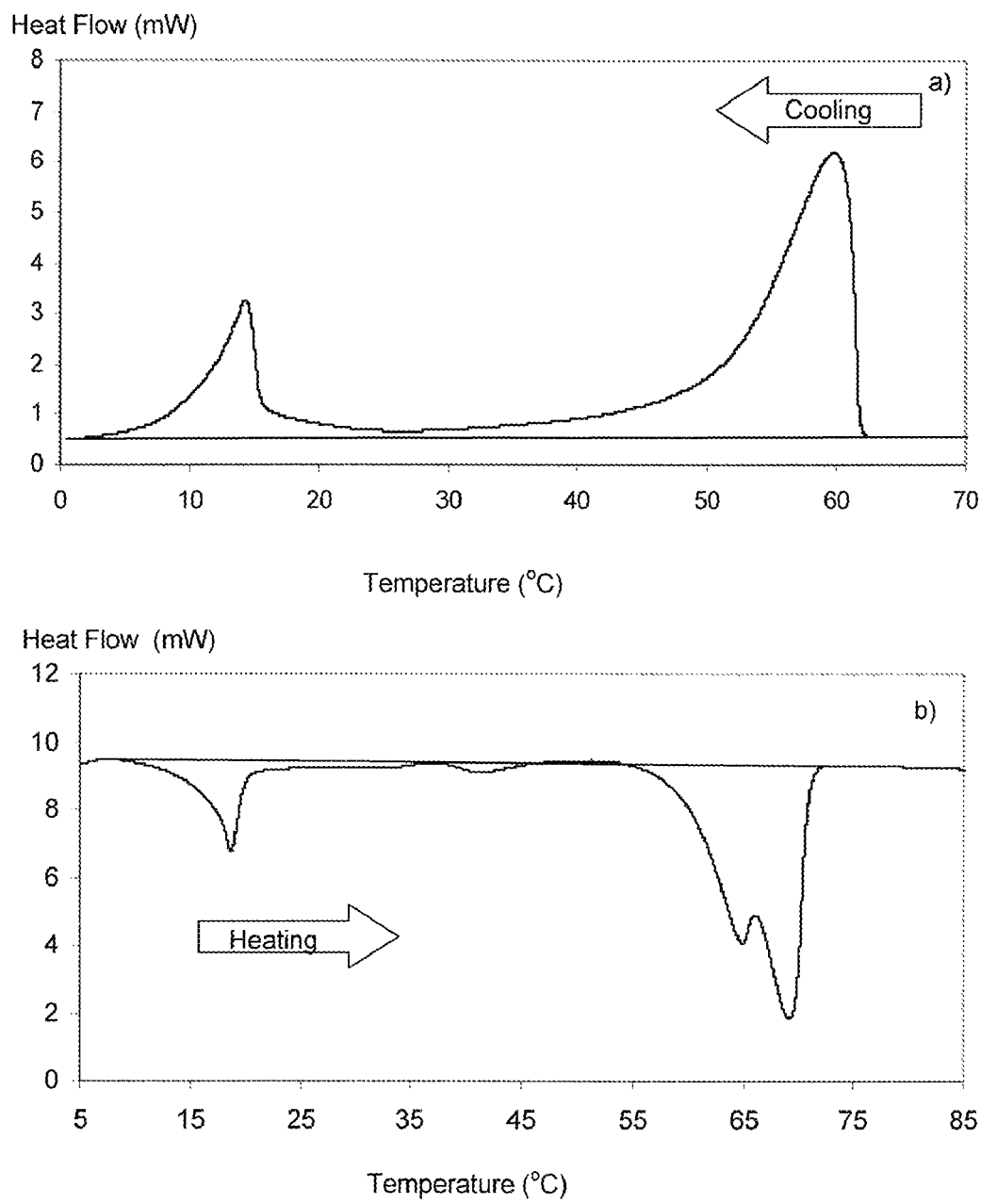
FIGS. 3a and 3b which show the cooling and subsequent heating behaviour respectively of a 5% w/w monoglyceride (Dimodan HP) sunflower oil dispersion using differential scanning calorimetry.

A 5% w/w monoglyceride (Dimodan HP, Danisco) sunflower oil dispersion was prepared at room temperature. The dispersion was heated in a Setaram Micro DSC III differential scanning calorimeter. Approximately 0.7 g samples were loaded into 1 cm$^3$ stainless steel cuvettes and scanned over the temperature range 0 to 99° C. at a rate of 0.5° C./minute against a sunflower oil reference. FIGS. 3a and 3b show the cooling and subsequent reheating curves respectively from which an exothermic event is observed on cooling as the monoglyceride crystallises from solution (FIG. 3a) and an endothermic event is observed on heating as the monoglyceride melts (FIG. 3b)

Example 4

Process for Making an Oil-in-water Emulsion with Oil Droplets Comprising a Chitosan Second Outer Layer on a Sucrose Ester First Inner Layer which has been Previously Partially Hydrolysed A one liter aqueous solution of 1% w/w sugar ester (Ryoto P-1670, Mitsubishi-Kagaku Foods Corporation, Japan) in 0.1% w/w potassium sorbate was prepared. To this 2 cm$^3$ of phosphoric acid was added to reduce the pH to 4.0. The solution was then heated to boiling and 500 cm$^3$ of this hot solution mixed with a palm oil blend (Creamelt 900, Loders Croklaan) to give the required oil content. Menthol was added to the oil phase prior to making the emulsion at a level to give 0.08% w/w menthol in the final emulsion. The mixture was homogenised using a Silverson LR4 mixer running at high speed for 30 seconds and the resulting emulsion held at 85° C. for two minutes. The emulsion was then allowed to cool and was stored at 4° C. The emulsion oil content was 20% w/w. The emulsion was washed with sterile distilled water to remove the excess sugar ester and then the pH changed to between 10-12 by the drop wise addition of 1 mol/dm$^{-3}$ NaOH in water. The emulsion then was centrifuged for 30 minutes at 5000 rpm in a Sorvall RC5C centrifuge in an 8×250 cm$^3$ rotor. The emulsion was then washed with sterile water until a pH of 6.8 was reached.

The emulsion was then mixed 50:50 w/w for 30 minutes with previously pasteurised 0.2% w/w chitosan aqueous solution (ChitoClear, Primex Ingredients ASA, Norway), containing 0.1% potassium sorbate, 2 cm$^3$/liter phosphoric acid and 150 mM NaCl at pH 4. After washing once with distilled water, the emulsion was centrifuged at 5000 rpm in a Sorvall RC5C centrifuge and the aqueous phase discarded. The emulsion was then mixed 50:50 w/w for 30 minutes with a previously pasteurised 0.2% w/w chitosan aqueous solution containing 0.1% potassium sorbate, 2 cm$^3$/liter phosphoric acid and 150 mM NaCl at pH 4. The excess chitosan solution was removed by centrifugation at 5000 rpm in a Sorvall RC5C centrifuge and the aqueous phase discarded and replaced by water. After washing extensively with distilled water the mixture was centrifuged and the aqueous phase discarded. The oil phase was then re-suspended to make a desired product.

A control emulsion was prepared in the same manner except that the pH of the washing solution was not increased to pH 11 prior to the chitosan solution being introduced.

Electrophoretic mobility measurements were carried out on a Malvern ZetaSizer Nano series instrument with back-scattering dynamic light scattering detection. The mobility data was used to calculate the zeta potential or surface charge density of the droplets. Samples were prepared by dilution in deionised water to approximately 1% by weight oil in order to make measurements. 1 ml of the prepared samples was loaded into the cuvettes and the data obtained at 25° C. The results were analysed using the Malvern DTS (Dispersion Technology Software). Table 1 shows the zeta potential for the two emulsions in which it can be seen that the alkali treatment has caused the zeta potential of the emulsion to be increased significantly (significantly more positively charged).

TABLE 1

Zeta potential measurement of the emulsions of example 4

| Sample | Zeta potential (mV) |
|---|---|
| Control emulsion | +10.6 |
| Alkali treated emulsion | +42.7 |

Flavour release was measured by an atmospheric pressure chemical ionisation mass spectrometry (APCI-MS) breath technique using a Navigator mass spectrometer fitted with APcl interface, and MassLynx and Xcalibur software. This technique measures the release of volatile (flavour) molecules into the nasal cavity from a food sample during a chewing process The technique involves gently sucking exhaled air from the nose into the mass spectrometer where the volatiles are detected as protonated $[M+H]^+$ ions. The subject sipped 2.5 ml of the sample and swilled it around in the mouth, swallowed it and then chewed at a rate of approximately 1 chew per second with a respiratory rate of between 6-8 breaths per minute for 5 minutes. After this time the panellist washed their mouth with water before taking a second sample. Each product was sampled in duplicate or triplicate. The obtained chromatograms were integrated and the mean area counts of each exhalation peak were plotted as a function of time and the results presented as time-intensity profiles. Results were obtained in duplicate.

Figure 4:
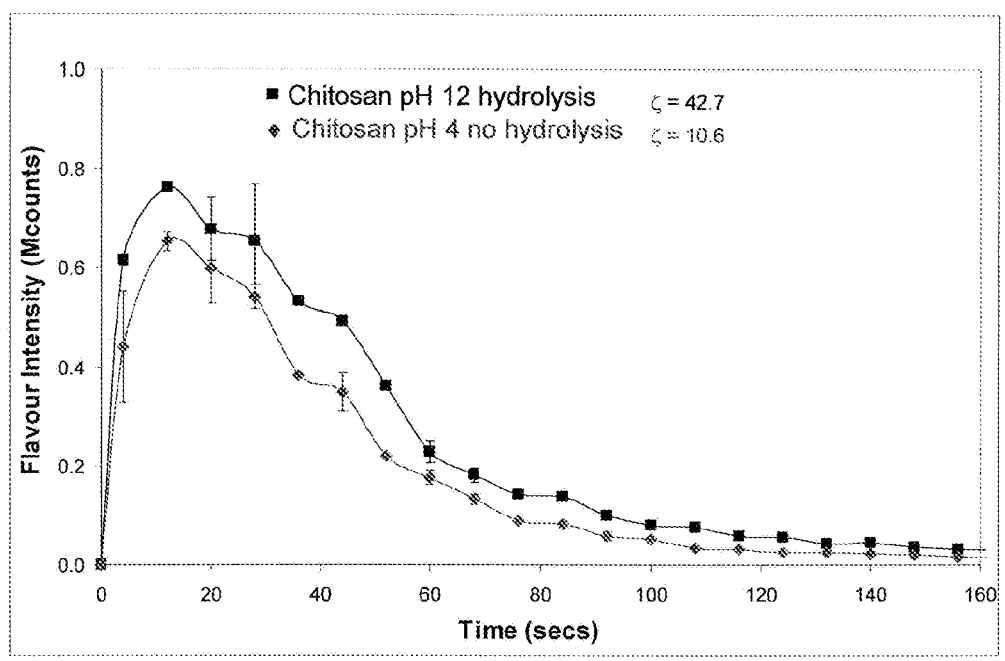
FIG. 4 which shows the flavour release from the sugar ester-chitosan stabilised emulsions prepared in example 4.

Further details of the technique can be found in "Atmospheric pressure chemical ionisation mass spectrometry for in-vivo analysis of volatile flavour release", Blake et al., Food Chem., 71(3), 327-338, (2000). The flavour release profiles for the emulsions are shown in FIG. 4 and show that the emulsion prepared with the alkali pre-treatment gives a more sustained release of menthol flavour. This result is consistent with the more positively charged emulsion particles interacting more favourably with the surfaces defined by the oral cavity.

Example 5

Process for Making an Oil-in-water Emulsion with Oil Droplets Comprising a Chitosan Second Outer Layer on a Monoglyceride Ester First Inner Layer which has been Previously Partially Hydrolysed A one liter aqueous solution of 1% w/w monoglyceride (Dimodan HP, Danisco) plus 0.05% w/w Polysorbate 60 (Tween 60, Uniquema) in 0.1% w/w potassium sorbate was prepared. To this 2 cm³ of phosphoric acid was added to reduce the pH to 4.0. The solution was then heated to 85° C. and 500 cm³ of the hot solution mixed with a palm oil blend (Creamelt 900, Loders Croklaan) to give the required oil content. The mix was homogenised using a Silverson LR4 mixer running at high speed for 30 seconds and the resulting emulsion held at 85° C. for two minutes. The mixture was then allowed to cool and stored at 4° C. The emulsion oil content was 20% w/w. The emulsion was then treated in identical fashion as set forth for example 4 and electrophoretic mobility measurements carried out on an emulsion according to the invention and a control prepared in the same manner except that the pH of the washing solution was not increased to pH 11 prior to the chitosan solution being introduced. Table 2 shows the zeta potential for the two emulsions in which it can be seen that the alkali treatment has caused the zeta potential of the emulsion to be increased significantly (significantly more positively charged).

TABLE 2

Zeta potential measurement of the emulsions of example 5

| Sample | Zeta potential (mV) |
|---|---|
| Control emulsion | −4.43 |
| Alkali treated emulsion | +17.8 |

Example 6

Process for Making an Oil-in-water Emulsion with Oil Droplets Comprising a Chitosan Second Outer Layer on a Palmitic Acid First Inner Layer which has been Previously Partially Hydrolysed An emulsion according to the invention and a control emulsion were prepared in the same manner as described hereinabove for example 5 except the 1% w/w monoglyceride was replaced by 1% w/w palmitic acid (Sigma PO500). Table 3 shows the zeta potential for the two emulsions in which it can be seen that the alkali treatment has caused the zeta potential of the emulsion to be increased significantly (significantly more positively charged).

TABLE 3

Zeta potential measurement of the emulsions of example 6

| Sample | Zeta potential (mV) |
|---|---|
| Control emulsion | +0.5 |
| Alkali treated emulsion | +32.0 |

Example 7

Process for Making an Oil-in-water Emulsion with Oil Droplets Comprising a Lysozyme Second Outer Layer on a Sucrose Ester First Inner Layer which has been Previously Partially Hydrolysed An emulsion according to the invention and a control emulsion were prepared in the same manner as described hereinabove for example 4 except the 0.2% w/w chitosan aqueous solution (ChitoClear, Primex Ingredients ASA, Norway), containing 0.1% potassium sorbate, 2 cm³/liter phosphoric acid and 150 mM NaCl at pH 4 was replaced by 0.2% w/w lysozyme aqueous solution. Table 4 shows the zeta potential for the two emulsions in which it can be seen that the alkali treatment has caused the zeta potential of the emulsion to be increased significantly (significantly less negatively charged). In this case the charge is still negative which may be due to the fact that the control emulsion had a much more negative charge.

TABLE 4

Zeta potential measurement of the emulsions of example 7

| Sample | Zeta potential (mV) |
|---|---|
| Control emulsion | −14.7 |
| Alkali treated emulsion | −4.4 |

The invention claimed is:

1. A stable emulsion comprising a droplet dispersed in an aqueous phase, the droplet comprising a core, a first inner layer coating the core, and a second outer layer coating the first inner layer, wherein the core comprises at least a liquid oil or gel oil continuous phase, wherein the first inner layer comprises at least one at least partially solid uncharged emulsifier and at least one anionic or cationic or zwitterionic emulsifier, the second outer layer comprises a first polycation or first polyanion or first polyzwitterion of opposing charge to the first inner layer, and wherein the at least partially solid uncharged emulsifier forms a solution in the aqueous phase or the liquid oil or the gel oil phase at temperatures greater than room temperature.

2. An emulsion according to claim 1, wherein the core is selected from the group consisting of a liquid oil, a gel oil, a water-in-liquid oil emulsion, a water-in-gel oil emulsion, a multiple emulsion wherein the continuous phase is a liquid oil or a gel oil, and a liquid oil or gel oil continuous phase dispersion.

3. An emulsion according to claim 1, wherein the liquid oil or gel oil continuous phase is selected from the group consisting of vegetable oil, animal oil, mineral oil and synthetic oil.

4. An emulsion according to claim 1, wherein the at least partially solid uncharged emulsifier is at least partially crystalline.

5. An emulsion according to claim 1, wherein the at least partially solid uncharged emulsifier is selected from the group consisting of a sucrose ester, a (poly)-glycerol ester of a fatty acid and a sorbitan ester.

6. An emulsion according to claim 5, wherein the sucrose ester is of formula (I)

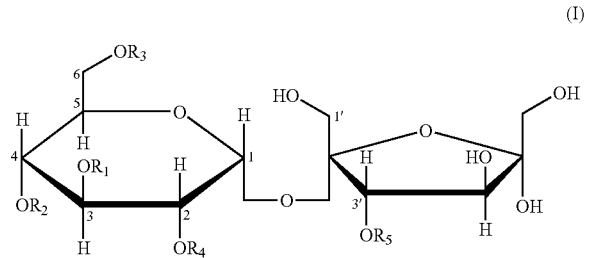

wherein $R_1$, $R_2$, $R_3$, $R_4$ and $R_5$ are independently from each other any non-toxic fatty acid radical.

7. An emulsion according to claim 1, wherein the anionic emulsifier is selected from the group consisting of stearic acid and palmitic acid.

8. An emulsion according to claim 1, wherein the cationic emulsifier is selected from the group consisting of cetyl trimethylammonium chloride, cetylpyridinium chloride, benzethonium chloride, hydroxypropyl guar hydroxypropyl trimonium chloride and guar hydroxypropyl trimonium chloride.

9. An emulsion according to claim 1, wherein the zwitterionic emulsifier is selected from the group consisting of a lecithin, cocamidopropyl betaine, dodecyl betaine, phosphatidyletholamine and phosphatidylcholine.

10. An emulsion according to claim 1 additionally comprising a third outer layer coating the second outer layer, the third outer layer comprising at least a second polyanion or at least a second polycation or at least a second polyzwitterion of opposing charge to the second outer layer.

11. An emulsion according to claim 1 wherein the first polyanion, is selected from the group consisting of alginate, carboxymethylamylose, carboxymethylcellulose, carboxymethyldextran, carageenan, cellulose sulphate, chrondroitin sulphate, chitosan sulphate, dextran sulphate, gum arabic, gellan gum, heparin, hyaluronic acid, pectin, amidated pectins, xanthan gum, proteins and glycoproteins.

12. An emulsion according to claim 1 wherein the first polycation is selected from the group consisting of chitosan, modified dextrans, hydroxymethylcellulose trimethylamine, lysozyme, polylysine, protamine sulphate, hydroxyethylcellulose trimethylamine and proteins.

13. An emulsion according to claim 10 wherein the second polyanion is selected from the group consisting of alginate, carboxymethylamylose, carboxymethylcellulose, carboxymethyldextran, carageenan, cellulose sulphate, chrondroitin sulphate, chitosan sulphate, dextran sulphate, gum arabic, gellan gum, heparin, hyaluronic acid, pectin, amidated pectins, xanthan gum, proteins and glycoproteins.

14. An emulsion according to claim 10 wherein the second polycation is selected from the group consisting of is selected from the group consisting of chitosan, modified dextrans, hydroxymethylcellulose trimethylamine, lysozyme, polylysine, protamine sulphate, hydroxyethylcellulose trimethylamine and proteins.

15. An emulsion according to claim 1 wherein the wherein the first inner layer comprises at least one at least partially solid uncharged emulsifier and at least one anionic emulsifier.

* * * * *